United States Patent
Hung et al.

(10) Patent No.: US 6,752,783 B2
(45) Date of Patent: Jun. 22, 2004

(54) SAFETY DEVICE FOR SYRINGE

(76) Inventors: Ming-Kan Hung, 11F-2, No. 43, Chai-I Street, Taichung City (TW); Chuang-Da Lee, 4F, No. 357, Da-Na Road, Su-Lin Area Taipei City (TW)

( * ) Notice: Subject to any disclaimer, the term of this patent is extended or adjusted under 35 U.S.C. 154(b) by 148 days.

(21) Appl. No.: 10/191,864

(22) Filed: Jul. 10, 2002

(65) Prior Publication Data

US 2004/0010234 A1 Jan. 15, 2004

(51) Int. Cl.⁷ ................................................ A61M 5/00
(52) U.S. Cl. ...................................... 604/110; 604/187
(58) Field of Search .................................. 604/110, 181, 604/187, 188, 192, 198

(56) References Cited

U.S. PATENT DOCUMENTS 4,801,295 A * 1/1989 Spencer ...................... 604/198
5,201,708 A * 4/1993 Martin ......................... 604/110
5,222,945 A * 6/1993 Basnight ...................... 604/110
5,415,645 A * 5/1995 Friend et al. ................ 604/110

* cited by examiner

Primary Examiner—Brian L. Casler
Assistant Examiner—Kevin C. Sirmons
(74) Attorney, Agent, or Firm—Charles E. Baxley

(57) ABSTRACT

A safety device for syringes includes a sleeve mounted to the barrel of the syringe and a connection member is movably received in the sleeve and two ends of the connection member are respectively and securely connected to a needle assembly and the barrel. The sleeve is slid toward the needle assembly to kick the cap off and then pulled back to expose the needle to proceed syringing. After finishing the syringing process, the sleeve is slid toward the needle assembly again to let the pawls of the connection member be securely engaged with the grooves of the sleeve and the needle is received in the sleeve.

7 Claims, 7 Drawing Sheets

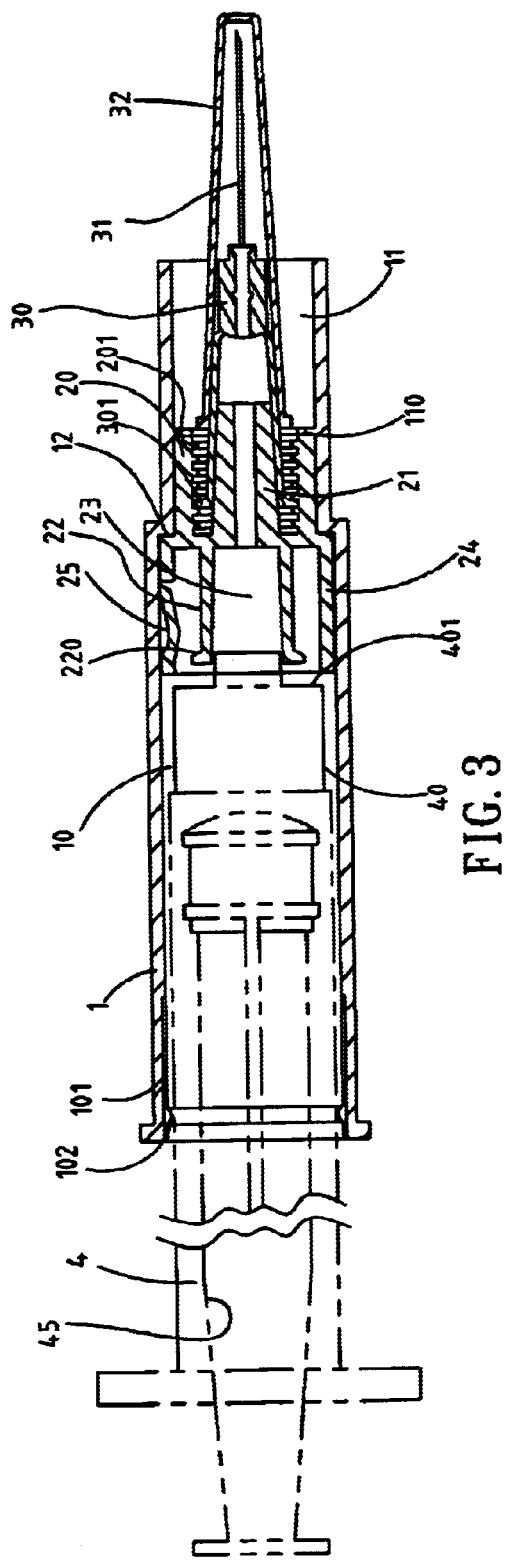
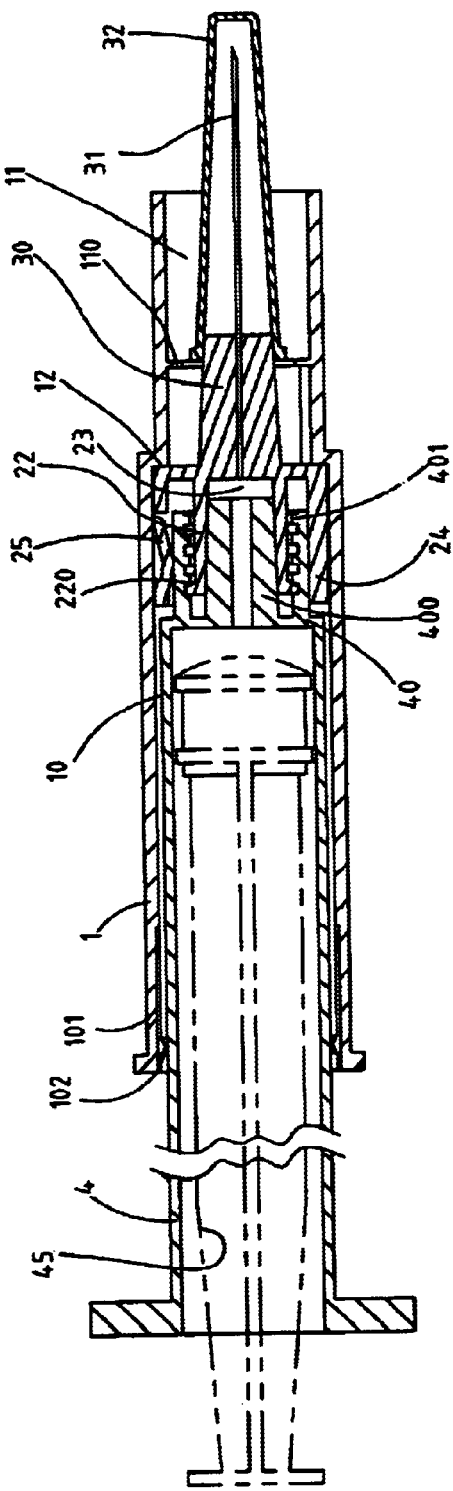
FIG. 3
FIG. 9

SAFETY DEVICE FOR SYRINGE

FIELD OF THE INVENTION

The present invention relates to a safety device for syringe and the device is slidably mounted to the barrel. The device is slidably operated to allow the needle extend from the device and receive the needle after being used.

BACKGROUND OF THE INVENTION

A conventional syringe device is shown in FIG. 1 and generally includes a barrel 10 with a plunger 15 movably received in the barrel 10. A stopper 17 is connected to an end of the plunger 15 by a hook 17 on the distal end of the plunger 15. A base 12 extends from the barrel and a needle assembly 18 is mounted to the base 12. The needle assembly 18 includes a needle hub 180 and the needle 181 is secured to the needle hub 180. A cap is mounted to the needle hub 180 to protect the user from being hurt by the needle 181. Medicine is received in the chamber 11 in the barrel 10 and is ejected out from the needle 181 by pushing the plunger 15. However, the users are often hurt by the needle 181 when re-capping the cap to the needle hub 180 and this is dangerous for the users. Besides, the caps could disengaged from the discarded syringes and the janitors could be hurt by the needles without the protection of the caps.

The present invention intends to provide a safety device which is slidably mounted to the barrel and the needle is received in the device after the syringe is used.

SUMMARY OF THE INVENTION

In accordance with one aspect of the present invention, there is provided a safety device for syringes and the safety device includes a sleeve having a first passage for receiving a connection member therein. A connection portion extends from a first end of the sleeve so as to form an inward shoulder. A plurality of grooves are defined in the inner periphery of the first passage and located at a second end of the sleeve. A plurality of protrusions extend inward from the inner periphery of the first passage of the sleeve.

The connection member has a base at a first end of the connection member and a second passage is defined through the connection member. A tubular wall extends from the first end of the connection member and the base is enclosed by the tubular wall. A skirt extends from an outer periphery of the tubular wall and a plurality of pawls split from the skirt. A first end of the connection member is connected to the barrel.

A needle assembly has a needle hub which is mounted to the base and securely engaged with the tubular wall. A needle extends from the needle hub and a cap is removably mounted to the needle hub.

The present invention will become more obvious from the following description when taken in connection with the accompanying drawings which show, for purposes of illustration only, a preferred embodiment in accordance with the present invention.

BRIEF DESCRIPTION OF THE DRAWINGS

FIG. 3 shows the needle assembly is connected to the connection member and the barrel is not yet connected to the connection member;

FIG. 9 shows that the needle assembly is made with the connection member as a one-piece element.

DETAILED DESCRIPTION OF THE PREFERRED EMBODIMENTS

Figure 1:
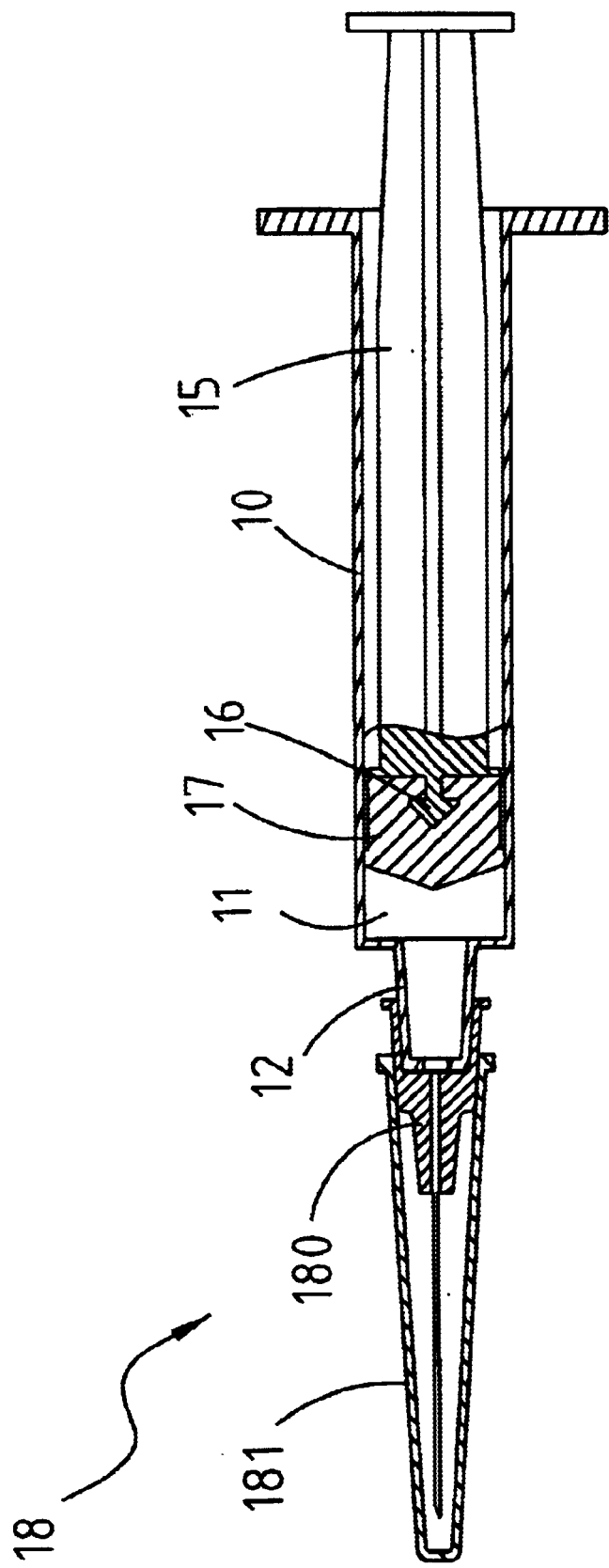
FIG. 1 is a cross sectional view to show a conventional syringe assembly.
Figure 2:
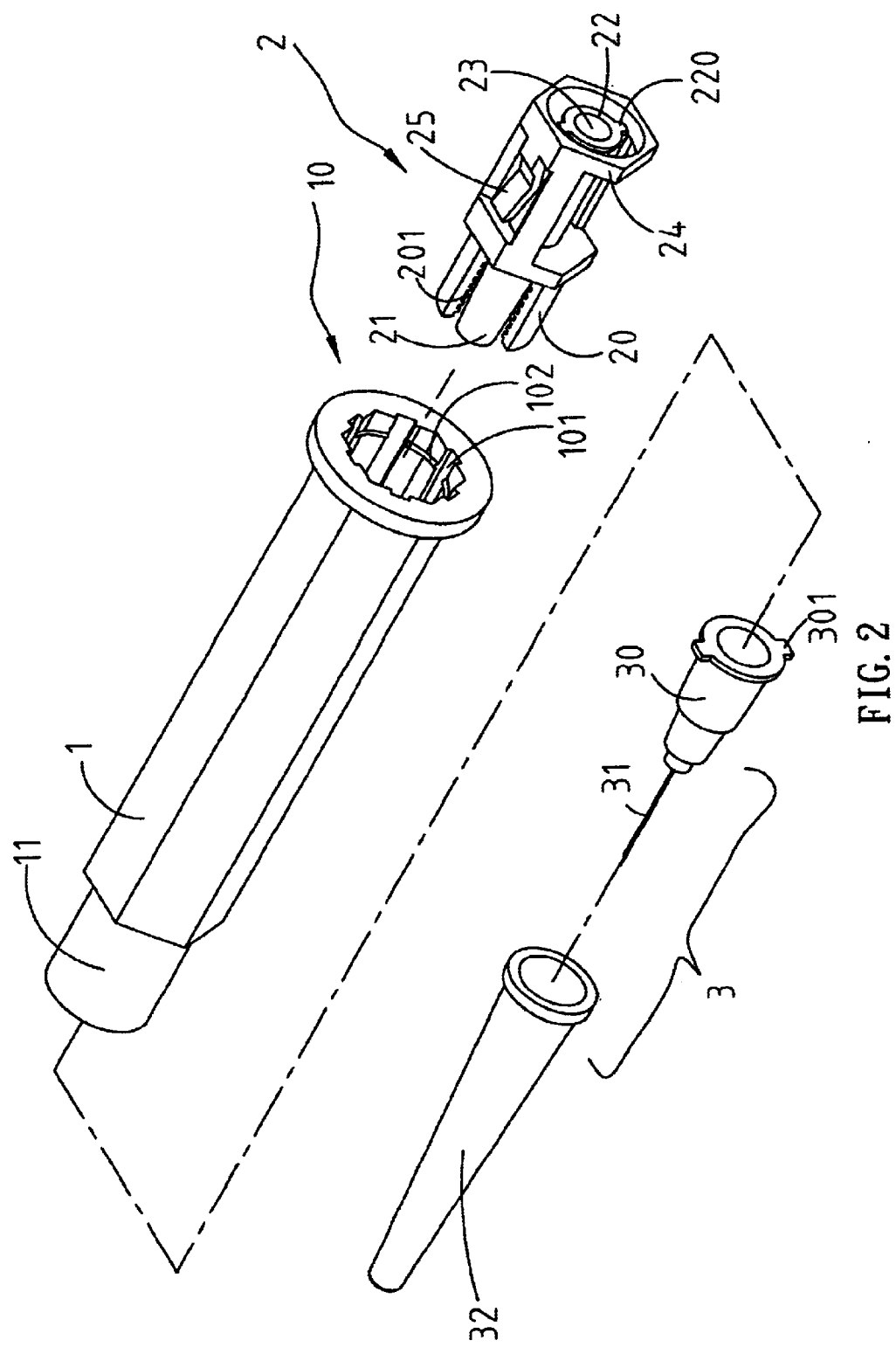
FIG. 2 is an exploded view to show the safety device of the present invention.

Referring to FIGS. 2 and 3, the safety device of the present invention comprises a sleeve 1 which has a first passage 10 defined therethrough with a polygonal inner periphery and a connection portion 11 extends from a first end of the sleeve 1. An inward shoulder 12 is defined in the inner periphery of the first passage 10 and the connection portion 11 communicates with the first passage 10 of the sleeve 1. A flange 110 extends from an inner periphery of the connection portion 11. A plurality of grooves 101 are defined in the inner periphery of the first passage 10 and located at a second end of the sleeve 1. A plurality of protrusions 102 extend inward from the inner periphery of the first passage 10 of the sleeve 1 and located between the grooves 101.

A connection member 2 is movably received in the first passage 10 of the sleeve 1 and has a base 21 at a first end of the connection member 2. A second passage 23 is defined through the connection member 2. A tubular wall 20 extends from the first end of the connection member 20 and the base 21 is enclosed by the tubular wall 20. A skirt 24 having a polygonal outer periphery extends from an outer periphery of the tubular wall 20 and a plurality of pawls 25 split from the skirt 24. The polygonal skirt 24 is non-rotatably received in the first passage 10 and stopped by the inward shoulder 12. The tubular wall 20 has a threaded inner periphery 201.

A needle assembly 3 has a needle hub 30 which is mounted to the base and securely engaged with the tubular wall 20. A needle 31 extends from the needle hub 30 and a cap 32 is removably mounted to the needle hub 30. In particulars, the needle hub 30 has two teeth 301 on an outer periphery thereof and the two teeth 301 of the needle hub 30 are threadedly engaged with the threaded inner periphery 201. The cap 32 has an end thereof stopped by the flange 110.

Figure 4:
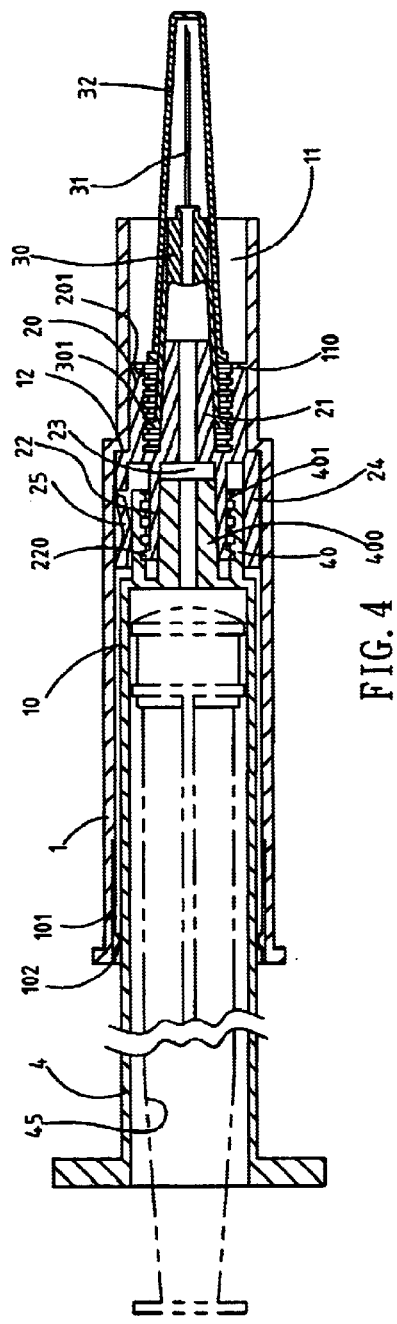
FIG. 4 shows that the barrel is connected to the connection member.

The sleeve 1 is slidably mounted to a barrel 4 of a syringe assembly and a plunger 45 is movably received in the barrel 4. A tongue 400 extends front a front end of the barrel 4 and a wall 40 extends from the front end of the barrel 4 and surrounds the tongue 400. An inner threaded surface 401 is defined in an inner periphery of the wall 40. The tongue 400 is inserted in the second passage 23 and the first end 22 of the connection member 2 has two teeth 220 on outer periphery thereof and the teeth 220 are threadedly connected to the inner threaded surface 401 of the barrel 4 as shown in FIG. 4. This connection can be done by simply rotating the barrel 4 because the connection member 2 is not rotatable in the sleeve 1.

Figure 5:
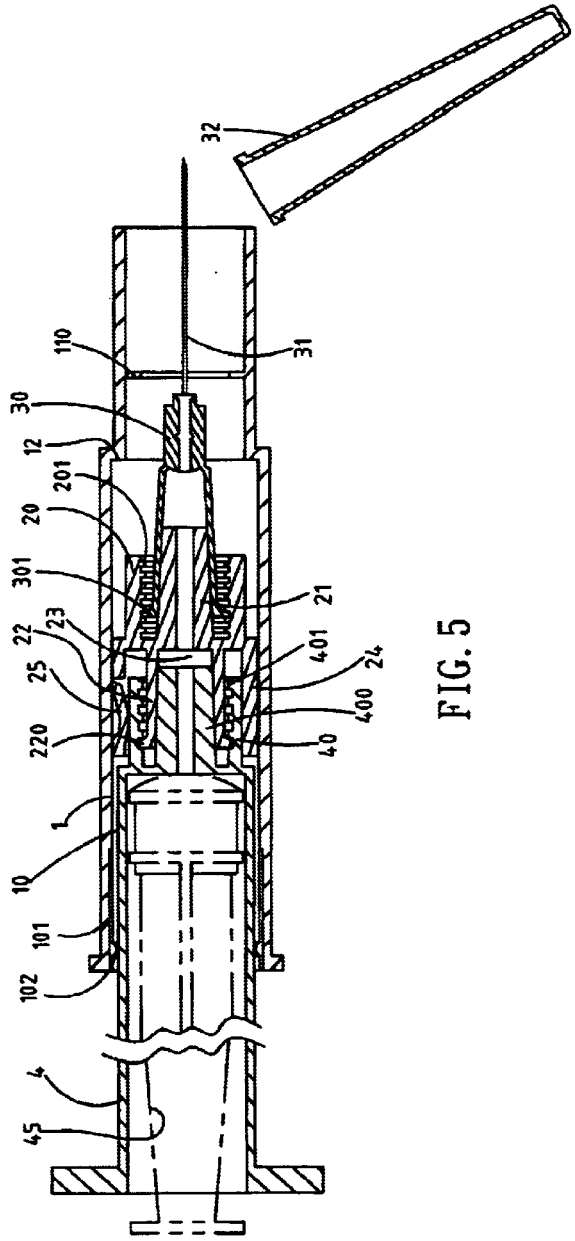
FIG. 5 shows that the cap of the needle assembly is kicked out by sliding the safety device toward the needle assembly.
Figure 6:
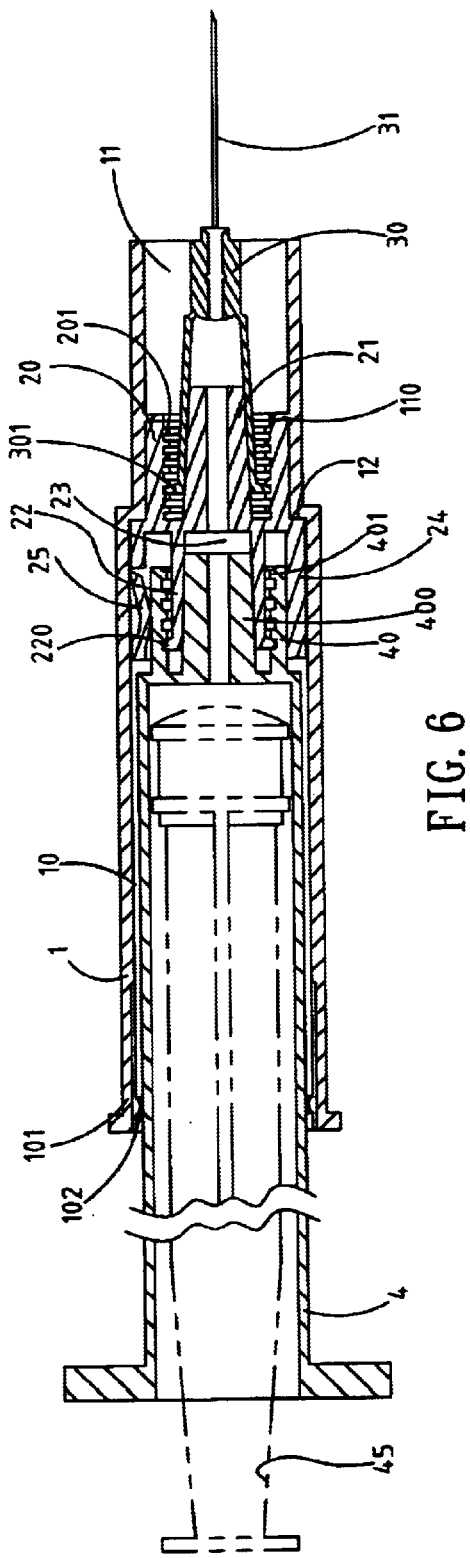
FIG. 6 shows that the needle is exposed from the safety device by sliding the sleeve backward.

As shown in FIG. 5, before proceeding syringing, the sleeve 1 is slid forward toward the needle assembly 3 till the cap 32 pushed by the flange 110 drops out from the sleeve 1. The sleeve 1 is then pulled backward as shown in FIG. 6 to let the needle 31 exposed so as to be ready for syringing.

Figure 8:
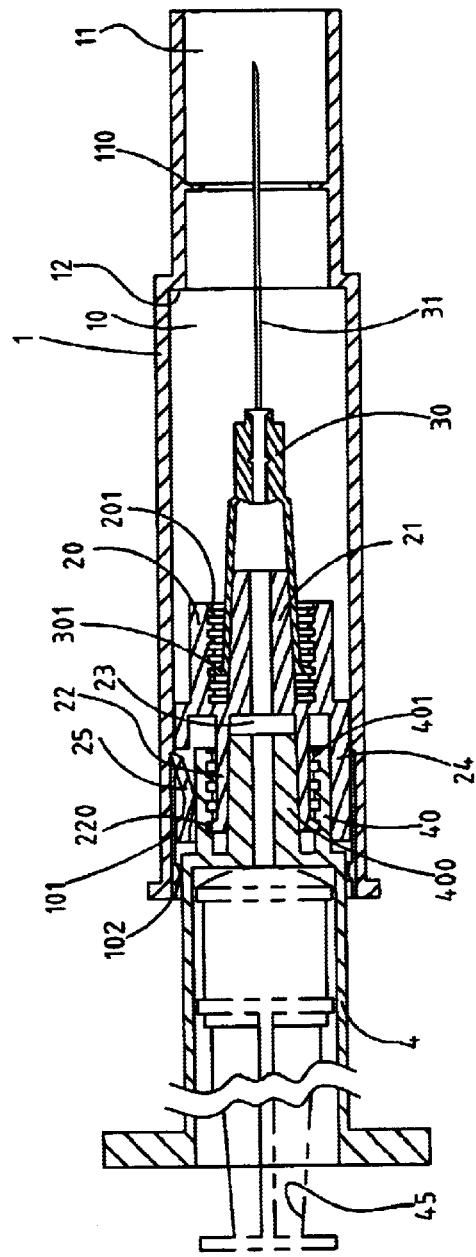
FIG. 8 shows that the needle is received in the sleeve and the pawls are engaged with the grooves in the sleeve.
Figure 7:
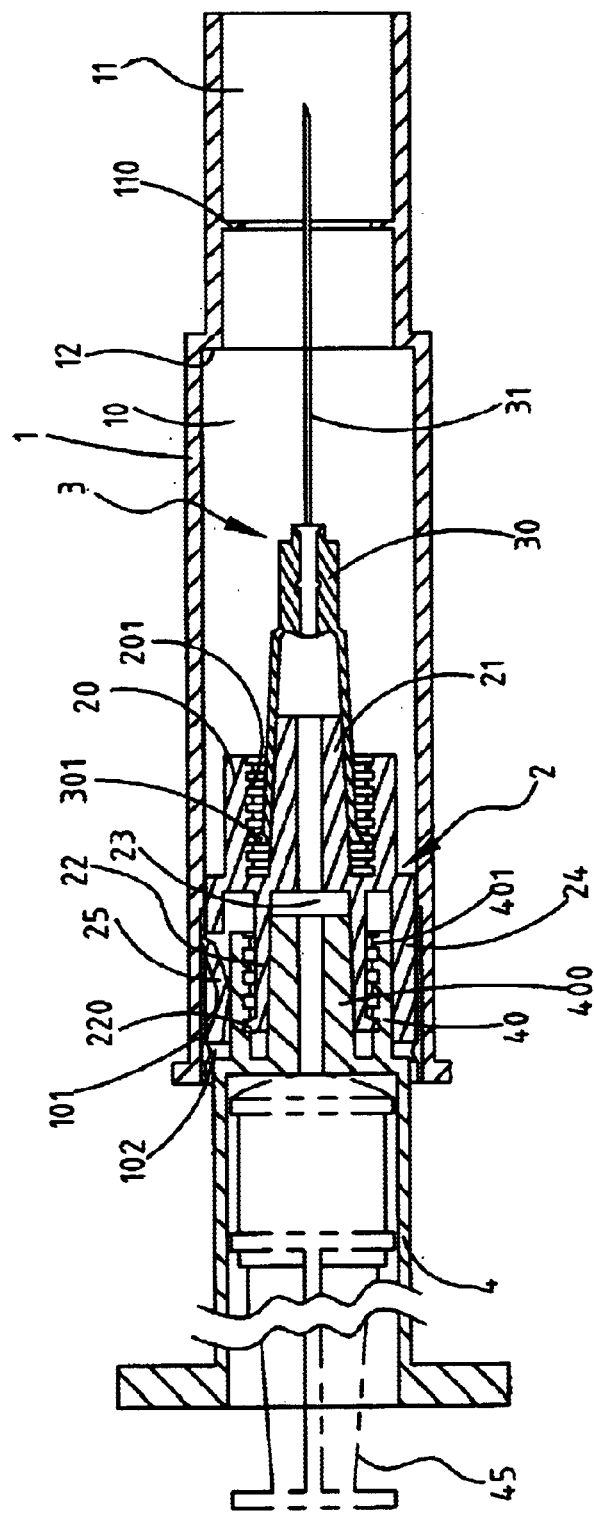
FIG. 7 shows that the pawls are pushed outward by the barrel when the sleeve is slid forward again after syringing.

After finishing the syringing process, the sleeve 1 is slid toward the needle assembly 3 again as shown in FIG. 7. Each of the pawls 25 has a convex portion extending toward away from the inner periphery of the first passage of the sleeve 1. During the sliding of the sleeve 1, the pawls 25 are pushed outward by the wall 40 of the barrel 4 till the pawls 25 are engaged with the grooves 101 of the sleeve 1, and the rear end of the skirt 24 is stopped by the protrusions 102 as shown in FIG. 8. Even if the sleeve 1 is pushed away from the needle assembly 3 again, the engagement between the pawls 25 and the grooves 101 ensures that the needle 31 will not extend from the sleeve 1 to hurt people.

FIG. 9 shows another embodiment wherein the needle assembly 3 can be made with the connection member 2 as a one-piece element.

Figure 10:
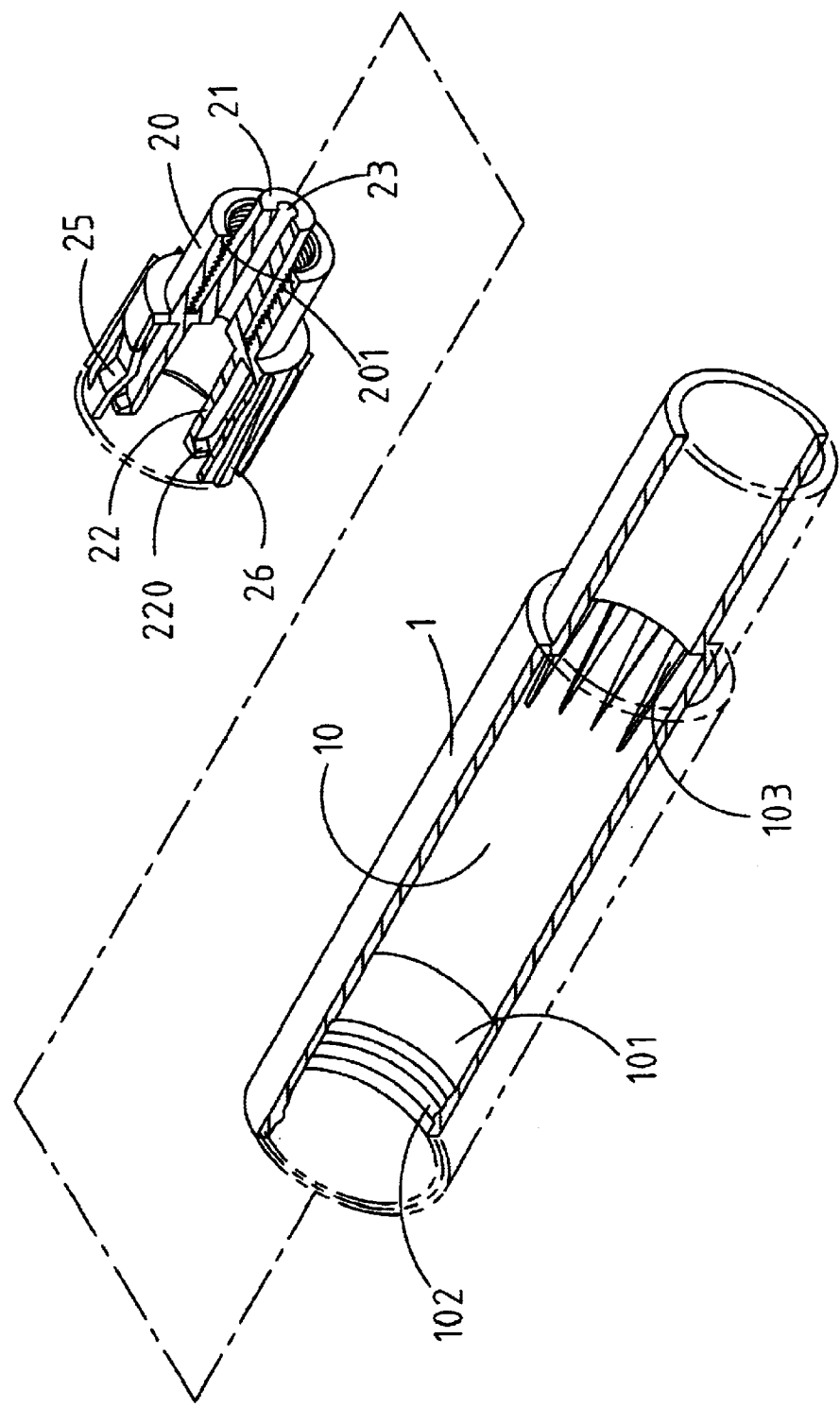
FIG. 10 shows that the sleeve and the connection member have ridges so as to prevent the connection member from rotating in the sleeve.

FIG. 10 shows yet another embodiment wherein the skirt of the connection member 2 has a circular outer periphery and a plurality of first ridges 26 extend from an inner periphery of the connection member 2. A plurality of second ridges 103 extend from the inner periphery of the first passage 10 of the sleeve 1. The first ridges 26 and the second ridges 103 are located alternatively when the connection member 2 are received in the sleeve 1 so as to prevent the connection member 2 from being rotated in the first passage of the sleeve 1.

The users do not touch the needle 31 before using the syringe or after finishing the process of syringing. The discarded syringe assembly ensures that the needle 31 do not hurt the users.

While we have shown and described the embodiment in accordance with the present invention, it should be clear to those skilled in the art that further embodiments may be made without departing from the scope of the present invention.

What is claimed is:

1. A safety device for syringes, comprising:

a sleeve having a first passage defined therethrough and a connection portion extending from a first end of the sleeve, an inward shoulder defined in an inner periphery of the first passage and the connection portion communicating with the first passage of the sleeve, a plurality of grooves defined in the inner periphery of the first passage and located at a second end of the sleeve, a plurality of protrusions extending inward from the inner periphery of the first passage of the sleeve;

a connection member movably received in the first passage of the sleeve and having a base at a first end of the connection member, a second passage defined through the connection member, a tubular wall extending from the first end of the connection member and the base enclosed by the tubular wall, a skirt extending from an outer periphery of the tubular wall and a plurality of pawls splitting from the skirt, a first end of the connection member adapted to be connected to the barrel, and a needle assembly having a needle hub which is mounted to the base and securely engaged with the tubular wall, a needle extending from the needle hub and a cap removably mounted to the needle hub.

2. The safety device as claimed in claim 1, wherein the first end of the connection member has two teeth on outer periphery thereof and the teeth are adapted to be connected to the barrel.

3. The safety device as claimed in claim 1, wherein the needle hub has two teeth on an outer periphery thereof and the tubular wall has a threaded inner periphery, the two teeth of the needle hub are threadedly engaged with the threaded inner periphery.

4. The safety device as claimed in claim 1, wherein a flange extends from an inner periphery of the connection portion and the cap mounted to the needle hub has an end of the cap stopped by the flange.

5. The safety device as claimed in claim 1 wherein the skirt of the connection member has a polygonal outer periphery and the first passage has a polygonal inner periphery so that the skirt of the connection member fits in the polygonal inner periphery of the first passage.

6. The safety device as claimed in claim 1, wherein the skirt of the connection member has a plurality of first ridges extending from an inner periphery of the connection member and a plurality of second ridges extend from the inner periphery of the first passage, the first ridges and the second ridges located alternatively so as to prevent the connection member from being rotated in the first passage of the sleeve.

7. The safety device as claimed in claim 1, wherein each of the pawls has a convex portion extending toward away from the inner periphery of the first passage of the sleeve.

* * * * *